(12) United States Patent
Nemoto et al.

(10) Patent No.: US 10,383,995 B2
(45) Date of Patent: Aug. 20, 2019

(54) SYRINGE HOLDING STRUCTURE

(75) Inventors: Shigeru Nemoto, Tokyo (JP); Takashi Saitoh, Tokyo (JP); Shigeru Muramatsu, Tokyo (JP); Hirofumi Uchizono, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 0 days.

(21) Appl. No.: 13/260,222

(22) PCT Filed: Mar. 26, 2010

(86) PCT No.: PCT/JP2010/055386
§ 371 (c)(1),
(2), (4) Date: Sep. 23, 2011

(87) PCT Pub. No.: WO2010/110429
PCT Pub. Date: Sep. 30, 2010

(65) Prior Publication Data
US 2012/0016234 A1    Jan. 19, 2012

(30) Foreign Application Priority Data

Mar. 27, 2009 (JP) .................................. 2009-078876

(51) Int. Cl.
*A61M 5/145* (2006.01)

(52) U.S. Cl.
CPC ..... *A61M 5/14546* (2013.01); *A61M 5/14566* (2013.01); *A61M 2005/14573* (2013.01)

(58) Field of Classification Search
CPC . G01S 5/0242; G01S 5/0252; G06Q 20/3224; G06Q 20/3276; G06Q 20/3278
See application file for complete search history.

(56) References Cited

U.S. PATENT DOCUMENTS

| | | | | |
|---|---|---|---|---|
| 5,520,653 | A | * | 5/1996 | Reilly et al. ................. 604/152 |
| 5,913,844 | A | * | 6/1999 | Ziemba et al. .............. 604/154 |
| 2001/0021821 | A1 | * | 9/2001 | Wang .................... A61M 5/322 604/110 |
| 2001/0021823 | A1 | | 9/2001 | Nemoto |
| 2002/0066715 | A1 | * | 6/2002 | Niedospial, Jr. ...... A61J 1/2096 604/415 |

(Continued)

FOREIGN PATENT DOCUMENTS

| | | |
|---|---|---|
| JP | 2002-011096 | 1/2002 |
| JP | 2004-357748 | 12/2004 |
| WO | WO2006059597 | * 6/2006 |

OTHER PUBLICATIONS

International Preliminary Report on Patentability for corresponding International Application No. PCT/JP2010/055386 dated Nov. 15, 2011.

*Primary Examiner* — Michael J Carey
*Assistant Examiner* — Shahdeep Mohammed
(74) *Attorney, Agent, or Firm* — Knobbe, Martens, Olson & Bear, LLP

(57) ABSTRACT

A syringe holding structure includes an adapter case (40) for holding a small-diameter syringe, and a syringe holding member having a flange-receiving groove (77) for holing flange portion (46) of the case(40). The syringe holding structure further includes locking mechanism for fixing the flange portion (46) in the groove (77) when the flange portion is inserted into flange-receiving groove and then it is rotated by 90 degrees about its axis.

9 Claims, 12 Drawing Sheets

(56) References Cited

U.S. PATENT DOCUMENTS

| | | | |
|---|---|---|---|
| 2004/0249276 A1* | 12/2004 | Nemoto | A61M 5/14546 600/432 |
| 2004/0254533 A1* | 12/2004 | Schriver | A61M 5/14546 604/131 |
| 2005/0283120 A1* | 12/2005 | Wang | A61M 5/3272 604/198 |
| 2009/0043257 A1 | 2/2009 | Cude | |
| 2009/0131756 A1* | 5/2009 | Nemoto | A61M 5/14546 600/300 |

* cited by examiner

SYRINGE HOLDING STRUCTURE

CROSS-REFERENCE TO RELATED APPLICATIONS

This application is the U.S. National Phase under 35. U.S.C. § 371 of International Application PCT/JP2010/055386, filed Mar. 26, 2010, which claims priority to Japanese Patent Application No. 2009-078876, filed Mar. 27, 2009The International Application was published under PCT Article 21(2) in a language other than English.

TECHNICAL FIELD

The present invention relates to a syringe holding structure for holding a syringe by holding a flange of the syringe, and more particularly, to a syringe holding structure on which any syringe can be easily mounted in a similar manner even when the syringes have different flange shapes.

BACKGROUND ART

Currently known medical imaging diagnostic apparatuses include CT (Computed Tomography) scanners, MRI (Magnetic Resonance Imaging) apparatuses, PET (Positron Emission Tomography) apparatuses and the like. For using the abovementioned apparatuses, a contrast medium, physiological saline or the like (hereinafter referred to as a chemical liquid) is often injected into the patient's body. Various types of injectors (chemical liquid injectors) which automatically perform the injection are commercially available.

Patent Document 1, for example, discloses a mechanism for holding a flange of the syringe as a mechanism for fixing the syringe to the injector. The flange of the syringe to be held by the mechanism has cut-portions on both sides of left and right and has two notches formed in its outer circumference (an arc-shaped portion).

The mechanism described in Patent Document 1 has a pair of hooks for engaging with the notches of the flange. To fix the flange on the mechanism, user first holds the syringe in the orientation in which the cut-portions of the flange are located on both sides of left and right, and then moves it downward so that the syringe is inserted between the pair of hooks. At this point, the pair of hooks have not come into the notches yet. Then, user rotates the syringe by 90 degrees about an axis, at that position, to cause the ends of the hooks to come into and engage with the notches thereby fixing the flange of the syringe.

Patent Document 1: Japanese Patent Laid-Open No. 2002-11096

DISCLOSURE OF THE INVENTION

In the mechanism disclosed in Patent Document 1, the way of fixing syringe is extremely simple since it can be achieved only by rotating the syringe by 90 degrees as described above. However, it is desirable that a syringe of a type having no notches formed on a flange thereof can also be mounted with a simple method.

The present invention has been made in view of the abovementioned problem, and it is an object thereof to provide a syringe holding structure on which any syringe can be easily mounted in a similar manner even when syringes have different flanges shapes.

SUMMARY

To solve the abovementioned problem the embodiment of present invention provides:

A syringe holding structure, including:
an adapter case having a cylindrical portion into which a syringe is inserted and a flange portion formed at an end of the cylindrical portion in an axis direction;
a syringe holding member having a flange-receiving groove for holding the flange portion; and
a locking means for fixing the flange portion within the flange-receiving groove when the flange portion is inserted into the flange-receiving groove and then the flange portion is rotated by a predetermined angle about its axis.

A rear face of the flange portion of the adapter case may has a concave portion formed therein, a flange of the syringe being adapted to fit into the concave portion, the concave portion having a depth in a thickness direction of the flange portion.

In the syringe holding structure according to another aspect of the present invention, the syringe holding member further has protruding portion configured to substantially abut on a rear face of the flange of the syringe when the syringe is mounted on the syringe holding member via the adapter case, to thereby fix the position of the syringe with respect to the adapter case in an axis direction In the syringe holding structure according to another aspect of the present invention, the protruding portion is a pair of ribs formed on left side and right side of the syringe holding member, respectively,
the rear face of the flange portion of the adapter case has two vertical grooves formed thereon,
the ribs being configured to pass through the vertical grooves to avoid interference the ribs and the flange portion during inserting the flange portion into the flange-receiving groove, and
the two vertical grooves being configured to be oriented horizontally in a state in which the flange portion is rotated, so that the rib interferes with inside of the flange portion to thereby prevent removal of the flange portion, even when the flange portion is attempted to be removed from the flange-receiving groove.

In the syringe holding structure according to another aspect of the present invention, an outer circumference of the flange portion of the adapter case has two notches formed thereon,
the lock means is a pair of plate springs with hook portion, provided with the syringe holding means, and
the hook portions are configured to engage with the notches to hold the flange portion when the flange portion is rotated by 90 degrees in the flange-receiving groove.

As described above, according to the present invention, it is possible to provide the syringe holding structure on which any syringe can be easily mounted in a similar manner even when the syringes have different flanges shapes.

DETAILED DESCRIPTION

An embodiment of the present invention will hereinafter be described with reference to the drawings.

Figure 1:
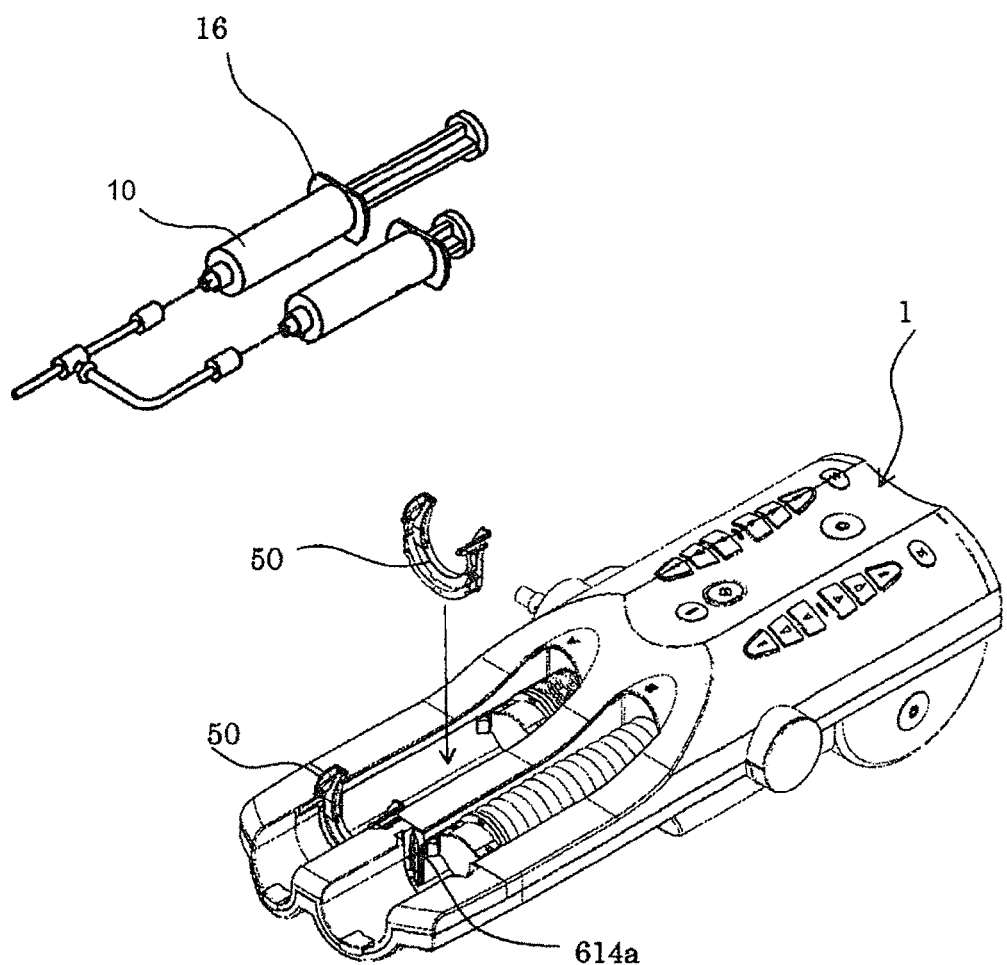
FIG. 1 is a perspective view showing an example in which a syringe holding structure according to one embodiment of the present invention is applied to an injector.
Figure 2:
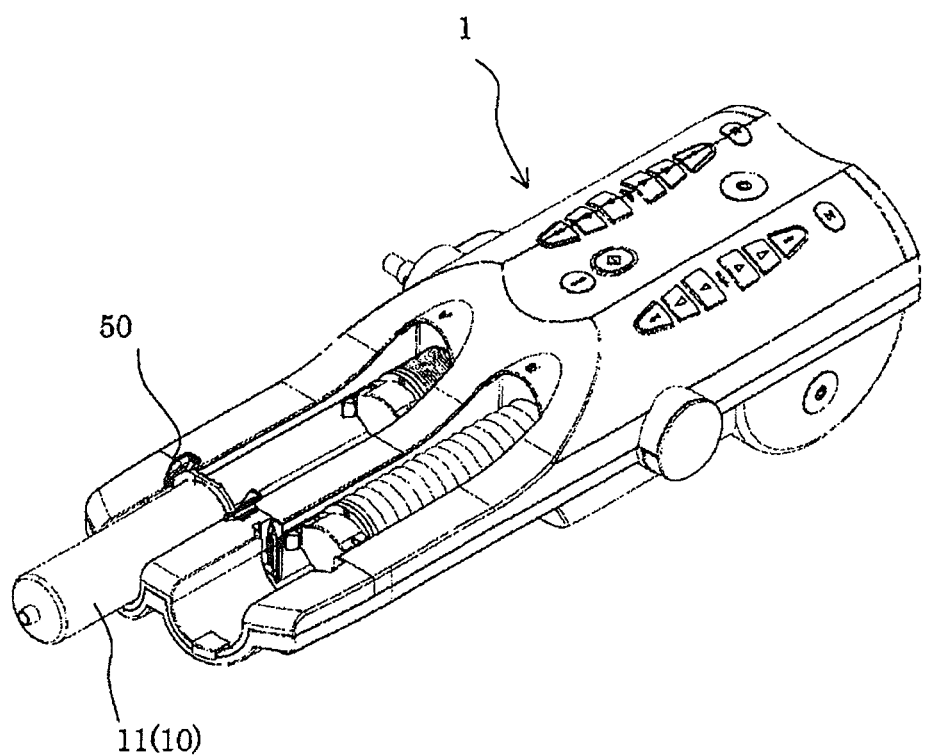
FIG. 2 is a perspective view showing the state in which a syringe is fixed in the injector.

An Injector 1 shown in FIG. 1 and FIG. 2 includes a syringe holding portion for holding a syringe, and piston driving mechanisms for pushing a piston member of the syringe into a cylinder member, and the like. The injector 1 automatically injects a chemical liquid from the syringe. Syringe 10 is intended to be directly mounted on the injector 1, whereas a syringe with smaller diameter (described below in detail) is intended to be mounted via a syringe holding member 50. Although not limited particularly, the syringe holding member 50 may be removable from the injector 1 in this example (described later in detail).

Figure 3:
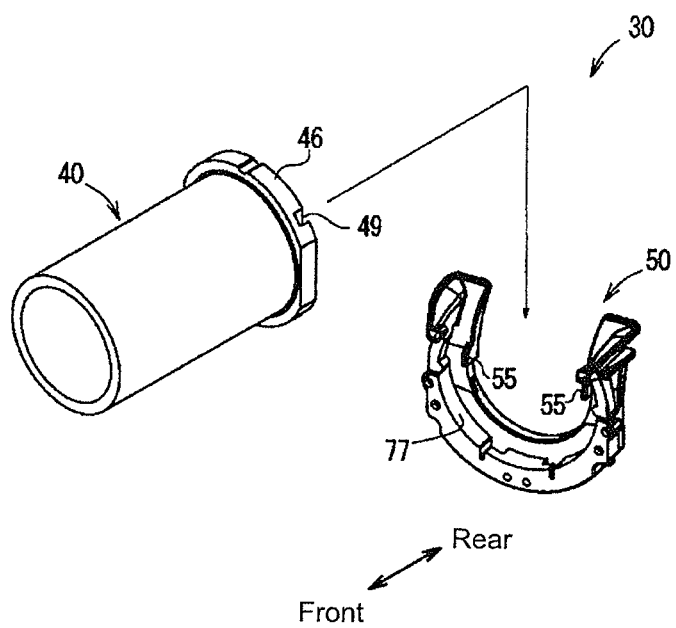
FIG. 3 is a perspective view showing the syringe holding structure according to one embodiment of the present invention.

A syringe holding structure according to the present embodiment has the syringe holding member 50 as one of components. As shown in FIG. 3, the syringe holding structure 30 includes an adapter case 40 formed in substantially tubular shape as a whole, and a syringe holding member 50 for holding flange portion 46 of the case 40.

Figure 4:
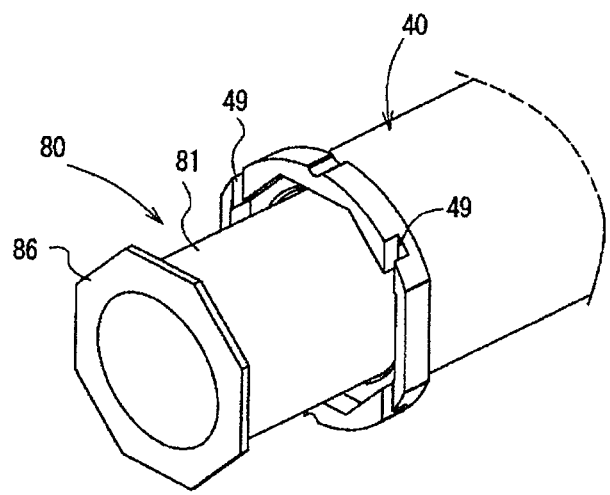
FIG. 4 is a perspective view showing the insertion of the syringe into an adapter case.

The adapter case 40 is used for mounting a syringe 80 (see FIG. 4), having a smaller diameter than that of syringe 10 in FIG. 1 on syringe holding member 50. The small-diameter syringe 80, as shown in FIG. 4, has a cylinder member 81 configured to be filled with a chemical liquid, and a piston member (not shown) slidably inserted into the cylinder member, like typical syringes. A flange 86 having polygonal outline shape (for example, octagon) is formed at a rear end of the cylinder member 81.

The syringe 80 may be of pre-filled type which is previously filled with a chemical liquid. Or, the syringe may be of a type in which a chemical liquid is sucked into an empty syringe for use. The shape of flange 86 may not be limited to the polygon but may be an ellipse, for example.

Figure 5:
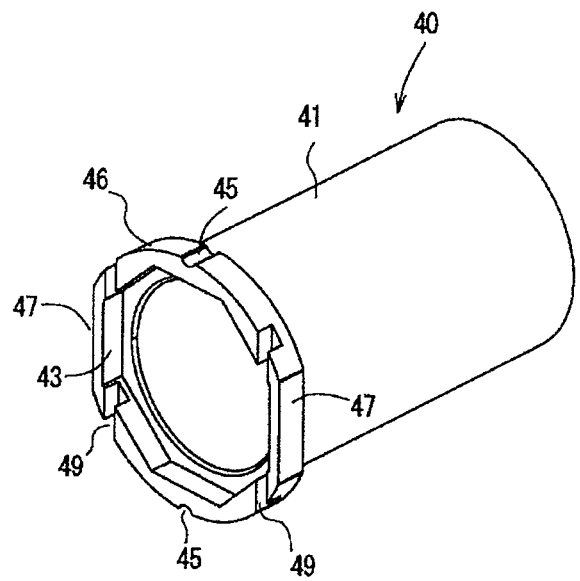
FIG. 5 is a perspective view showing the adapter case viewed from its base end side.
Figure 6:
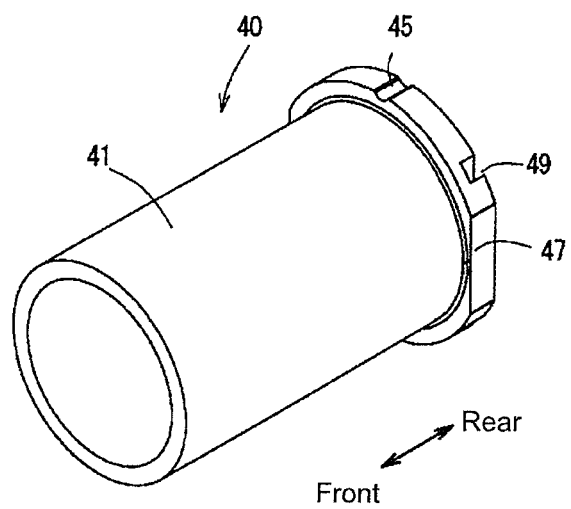
FIG. 6 is a perspective view showing the adapter case viewed from its end side.

The adapter case 40, as shown in FIGS. 5 and 6, may be made of for example molded plastic, and be formed in substantially tubular shape as a whole. The adapter case 40 has a cylindrical portion 41 into which cylinder member 81 of syringe 80 (see FIG. 4) is inserted and a flange portion 46 formed at an end in an axis direction of cylindrical portion 41.

The flange portion 46 has a substantially circular outline shape as a whole. The flange portion 46 has vertically cut portions 47, 47 formed on left side and right side respectively, and notches 45, 45 formed at the top and bottom (in an arc-shaped portion) of the flange portion.

A concave portion 43, as shown in FIG. 5, is formed on the rear face of flange portion 46, into which the flange 86 (see FIG. 4) of small-diameter syringe 80 is inserted. The concave portion 43 is formed in a thickness direction of flange portion 46, and has octagonal outline shape to correspond to the outline shape of flange 86. When the flange 86 of syringe 80 is positioned within the concave portion 43, the positions of syringe 80 and adapter case 40 in a circumferential direction is fixed (that is, the syringe 80 is no longer rotatable with respect to the case 40).

Vertical grooves 49, 49, as shown in FIG. 5, are formed on the rear face of flange portion 46 at left side and right side respectively. The vertical groove 49 is formed at a predetermined depth from the rear face of flange portion 46. The vertical grooves 49, 49 prevent interference between the flange portion 46 and the ribs 55, 55 during insertion of the flange portion 46 into the flange-receiving groove 77 (see FIG. 7) as later described.

Figure 7:
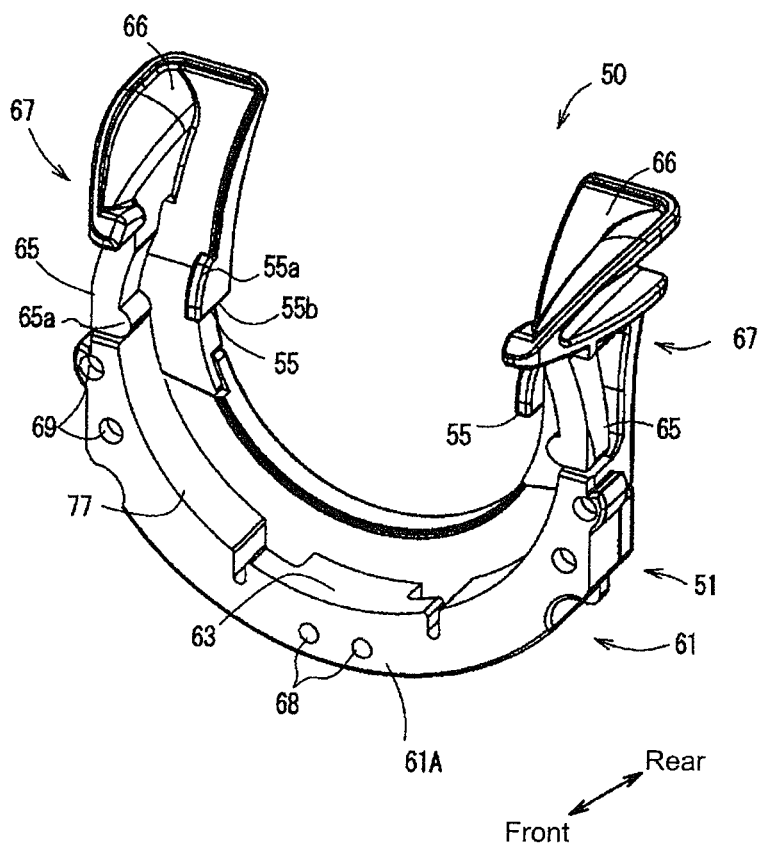
FIG. 7 is a perspective view showing a syringe holding member.
Figure 8:
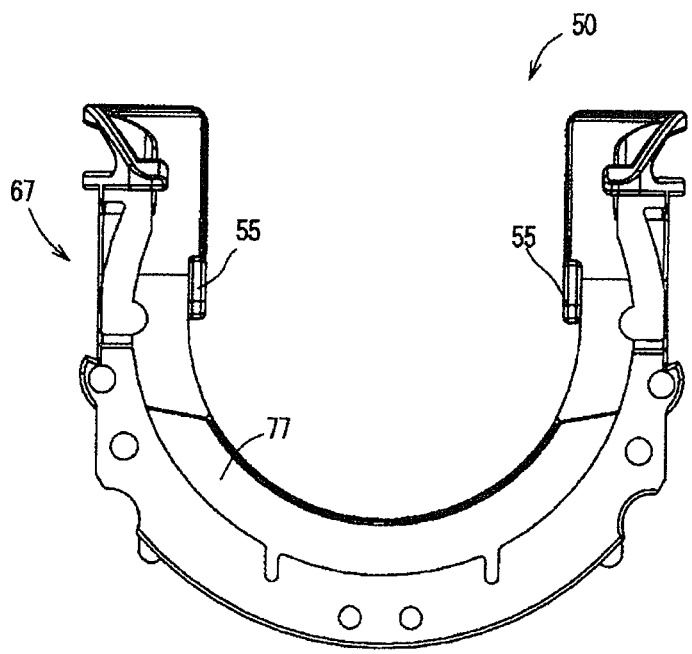
FIG. 8 is a front view showing the syringe holding member in FIG. 5.

FIG. 7 is a perspective view showing syringe holding member 50. FIG. 8 is a front view thereof. The syringe holding member 50 is formed in substantially U-shape as a whole and has a flange-receiving groove 77 with substantially U-shape for holding the flange portion 46 of adapter case 40.

It should be noted that both of the flange portion 46 of adapter case 40 and the flange 16 of syringe 10 may be engaged within the flange-receiving groove 77. Alternatively, only the flange portion 46 of adapter case 40 may be mounted but flange 16 of syringe 10 may not be mounted in flange-receiving groove 77.

As shown in FIG. 7, the syringe holding member 50 has an arc-shaped base member 51 forming a curved portion in a lower half of the U-shape (to be precise, forming substantially half of rear side portion in a thickness direction of the lower half), and a U-shaped movable member 61 attached at the front of the base member 51.

Both members are secured to each other by screws (by way of example) at two screw holes 68, 68 provided in a lower portion of the movable member 61. The movable member 61 has a fixing portion 61A occupying a certain area near the two screw holes 68, and a pair of arm portions 67, 67 extending upward from both sides of fixing portion 61A respectively. The arm portions 67, 67 are elastically bendable to thereby increase or decrease its distance therebetween. For example, when a user pinches the ends of arm portions 67, 67 by his fingers to bring them closer to each other, the arm portions 67, 67 are elastically deformed inward. When the user releases fingers on the arm portions 67, 67, they return to the original shape.

Each arm portion 67 is provided with a hooked plate spring 65 closer to the end. The hooked plate spring 65 is supported at its top end as a cantilever and extends downward. A hook portion 65a protruding inward in a diameter direction is formed at the end of plate spring 65. The hook portions 65a, 65 are configured to engage with notches 45, 45 (see FIG. 5) on flange portion 46 of adapter case 40, to allow the fixing of the flange portion 46 within the flange-receiving groove 77 (described below in detail). Such a fixing method is known for example in Japanese Patent Laid-Open No. 2002-11096.

A guide portion 66 gradually widened upward is formed on the top end of each arm portion 67 to allow the smooth guide of the flange portion into the groove. Particularly, in the present embodiment, the guide portion 66 is formed with a sufficient size both in the thickness direction (from front to back) and in horizontal direction of the flange portion, so that the flange portion can be inserted easily into the groove. Examples of the materials of base member 51 and/or movable member 61 may include: polyamide, polycarbonate, polyacetal, resin such as ABS. Metal material such as phosphor bronze may be used. Both members may be made of resin material or metal material, or one of them may be made of resin material and the other may be made of metal material.

The flange-receiving guide 77, as shown in FIG. 7, is formed inside of the arm portions 67, 67 and the fixing portion 61A. FIG. 7 shows the structure in which only the surface of flange-receiving groove 77 toward the back exists but any side face toward the front does not exist. The front surface may be a surface provided on the injector (not shown). In this case, the surface on the injector and the inner surfaces of the movable member and the like in FIG. 7 may cooperate to form the flange-receiving groove 77, which has substantially U-shape as a whole with a concave cross section. Particularly, when the front surface is formed on the member made of, for example, metal with sufficient rigidity, the flange portion 46 can be received favorably, since the member is not easily deformed or broken even when the flange portion 46 is pushed frontward during an injection of the chemical liquid.

As shown in FIG. 7, ribs 55, 55 are formed within the flange-receiving groove 77, somewhat inside from an intermediate portion of the arm portion 67. Each rib 55 extends to protrude frontward from the rear face of flange-receiving groove 77. Each rib 55 has a shape in which its protruding amount is larger on a lower side. In this example, an outline 55a of the rib 55 has a quarter-arc shape. The lower side of rib 55 is a substantially horizontal straight portion 55b.

Figure 9:
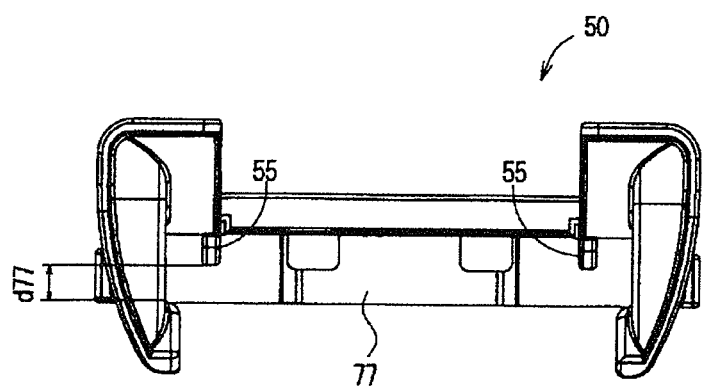
FIG. 9 is a plan view showing the syringe holding member in FIG. 5.
Figure 10:
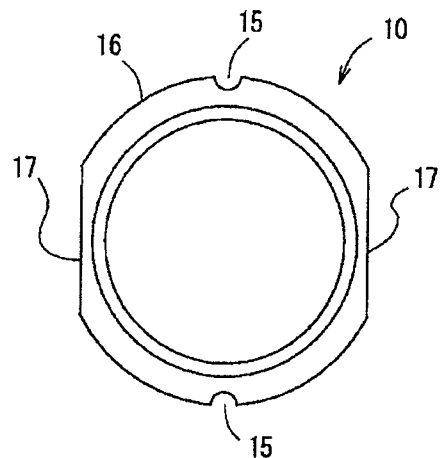
FIG. 10 is a diagram showing the flange shape of the syringe in FIG. 1.

As shown in FIG. 9 (plan view), the ribs 55, 55 makes narrow gaps d77 in the flange-receiving groove 77 into which the flange portion is inserted. The dimension of gap d77 is designed to be smaller than the thickness of flange portion 46 (see FIG. 5) of adapter case 40. Thus, flange portion 46 can be inserted into flange-receiving groove 77 only in a predetermined orientation.

As shown in FIG. 7, each arm portion 67 is provided with two concave portions 69 at its substantially intermediate portion in a length direction, and four concave portions are provided in total for the syringe holding member. Magnets placed within the concave portions 69 in a predetermined arrangement allow the identification of the type of syringe holding member 50 (for example, for a syringe of how many milliliters or the like), by using the difference of the polarities or the like. To realize this, a sensor (not shown) for detecting the polarity of the magnet may be provided for injector 1 (see FIG. 1). As a specific example, it is possible to detect syringe holding member 50 for a syringe of 200 ml when the N polarity is found on top and bottom, 100 ml when the S polarity is found on top and bottom, 50 ml when the N polarity and the S polarity are found on top and bottom, or another size when the S polarity and the N polarity are found on top and bottom.

Figure 11:
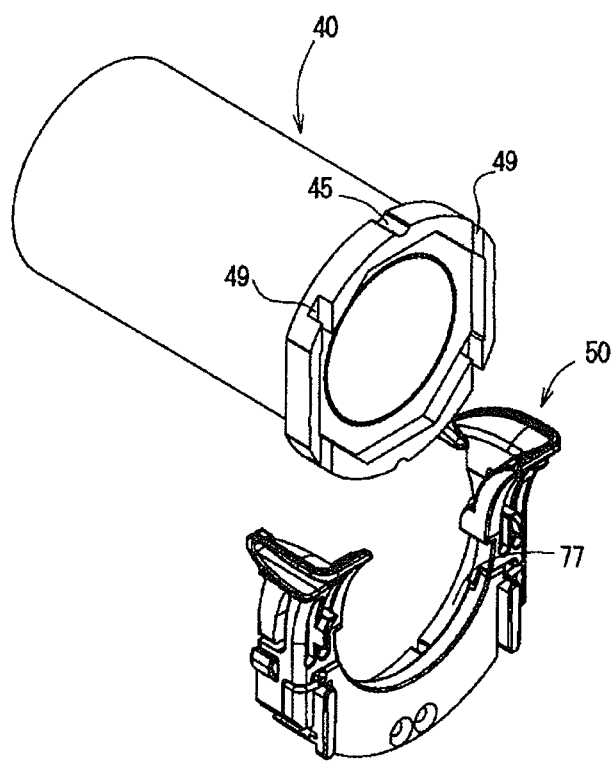
FIG. 11 is a diagram for explaining the procedure for mounting the adapter case on the syringe holding member (before mounting).
Figure 12:
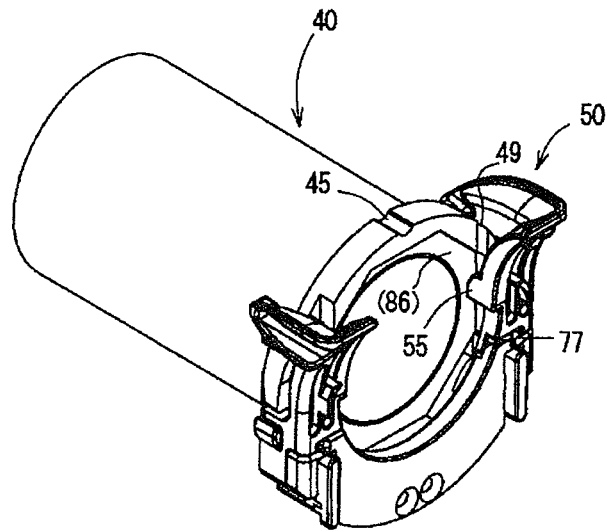
FIG. 12 is a diagram for explaining the procedure for mounting the adapter case on the syringe holding member (insertion).
Figure 13:
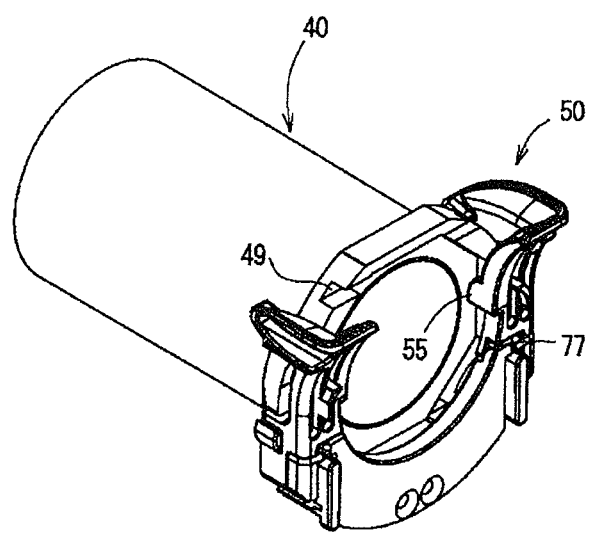
FIG. 13 is a diagram for explaining the procedure for mounting the adapter case on the syringe holding member (fixing).

Description will be made of the procedure of mounting the adapter case in the syringe holding structure of the present embodiment constructed as above. While FIG. 11 to FIG. 13 are referenced in the following description, the illustration of the syringe in the adapter case 40 is omitted in these figures.

First, the small-diameter syringe 80 is set in the adapter case 40 as shown in FIG. 4. When the flange 86 of syringe 80 is fitted into the concave portion 43 of adapter case 40, position of syringe 80 (in the circumferential direction) relative to the adapter case 40 is locked. Such a construction is advantageous in that it eliminates the need to provide a special configuration for fixing the positions of syringe 80 and adapter case 40 in the circumferential direction.

Next, the syringe 80 set on adapter case 40 is mounted on the syringe holding member 50. Specifically, as shown in FIG. 11, user holds the adapter 40 in the orientation in which the vertical grooves 49, 49 of flange portion 46 of case 40 are vertical, and then as shown in FIG. 3, user inserts the flange portion 46 of the case into the receiving groove 77 of syringe holding member 50.

During this procedure, since the ribs 55, 55 (see FIG. 5) of syringe holding member 50 can pass through the vertical grooves 49, 49, respectively, the flange portion 46 can be inserted smoothly into the receiving groove 77 without interference between the flange portion 46 and ribs 55.

Once the flange portion 46 is inserted in the receiving groove 77 (see FIG. 12), tip of each of ribs 55, 55 abuts on the rear face of the flange 86 of syringe 80. Thus the position of syringe 80 relative to the adapter case 40 in the axial direction is fixed. Such a construction is advantageous in that the need to provide a special configuration for fixing the positions of syringe 80 and adapter case 40 in the axial direction can be eliminated.

Ribs 55 can be changed in various manners as long as they serve to fix the position of adapter case 40 in the axial direction as described above. For example, rib may be a protrusion having a shape other than the rib. It is not necessary that the rib tip should abut on the rear face of the flange portion in the state in which the syringe 80 is mounted on syringe holding member 50. This is because the axial position of adapter case 40 can be substantially fixed even when the full abutment is not achieved.

After the insertion of the flange portion 46 into the receiving groove 77, the syringe is then rotated clockwise or counterclockwise as shown in FIG. 13 (90 degrees in this example). This causes the hook portions 65a, 65a of the plate spring to engage with two notches 45, 45 of outer circumference of flange portion 46 to thereby fix the flange portion 46 in the syringe holding member (in the circumferential direction).

To release the adapter case 40 from the syringe holding member 50 after the injection of chemical liquid, case 40 is rotated by 90 degrees clockwise or counterclockwise to disengage the hooks thereby removing the flange portion 46 from the flange-receiving groove 77.

In the state in which the adapter case 40 is mounted on syringe holding member 50, two vertical grooves 49, 49 in the rear face of the flange portion of the case are horizontally oriented. As a result, even when user attempts to the lift adapter case 40 upward to remove the flange portion 46 from the flange-receiving groove 77 in this state, the lower sides of ribs 55, 55 interfere with the inside of flange portion 46 (inner circumference of concave groove 43) and flange portion 46 cannot be released.

As described above, according to the present embodiment, even when syringe 80 is of the type having flange 86 of the octagonal outline shape (by way of example), having no notches in the outer circumference of the flange as shown in FIG. 4, the syringe 80 can be mounted on the syringe holding member 50 via the adapter case 40. In addition, the attachment method is extremely simple since the necessary steps are to insert the flange portion 46 of adapter case 40 into the flange-receiving groove 77 and to rotate it by 90 degrees.

It is not necessary to provide a special configuration for fixing the positions of syringe 80 and adapter case 40 in the axial direction, since while the syringe 80 is mounted, the ribs 55, 55 of syringe holding member 50 may abut on the rear face of flange 86 of syringe 80 to fix the positions of adapter case 40 and syringe 80 in the axial direction.

In the state in which adapter case 40 is mounted on syringe holding member 50, the vertical grooves 49 are horizontally oriented, and the ribs 55, 55 interfere with the inside of flange portion 46 to prevent the removal of flange portion 46 from syringe holding member 50. This can prevent the syringe from being detached during the injection of chemical liquid. Especially, the ribs 55, 55 also have a function of fixing the position of syringe 80 in the axial direction to case 40. The Ribs 55, 55, having several functions in this manner, can contribute to the simplified structure of the syringe holding member 50.

The present invention is not limited to the embodiment described above. For example, after the flange portion 46 is inserted into the flange-receiving groove 77, the syringe may be rotated by a predetermined angle other than 90 degree to fix flange portion 46 in flange-receiving groove 77.

The locking means for fixing flange portion 46 in flange-receiving groove 77 is not limited to the pair of hooked plate springs 65, 65 shown in FIG. 7, but other various types of mechanisms can be used.

[Other Embodiments]

Figure 14:
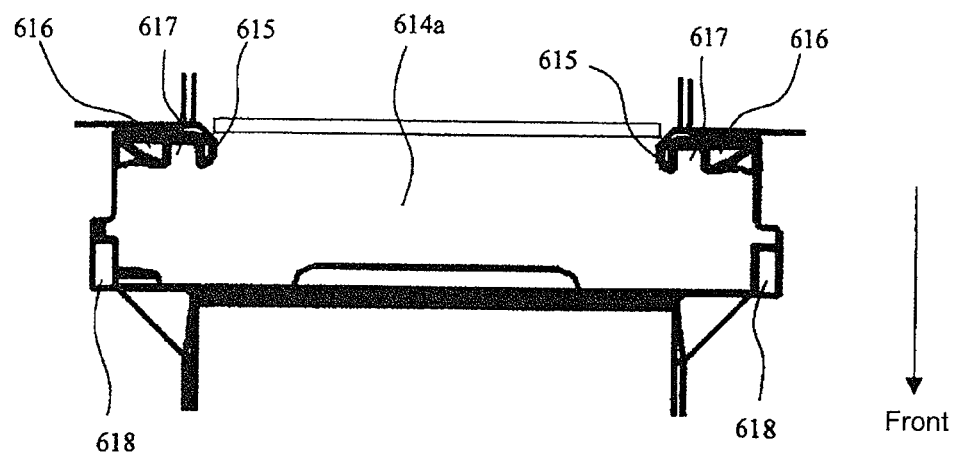
FIG. 14 is a plan view showing an adapter receiver provided for the injector.

While the embodiment has been described that the syringe holding member 50 is removably mounted on injector 1 as shown in FIGS. 1 and 2, the specific structure of the portion for receiving the syringe holding member 50 will hereinafter be described. As shown in FIG. 14, an adapter receiver 614a of U-groove shape for mounting syringe holding member 50 is formed in an upper surface of injector 1.

As shown in FIG. 14, the adapter receiver 614a has guide grooves 617 formed in a vertical direction at both sides in order to guide the insertion of the syringe holding member 50. Each guide grooves 617 extends between two ribs 615, 616 formed on the inner surface of adapter receiver 614a to extend in the insertion direction (vertical direction) of the syringe adapter.

Figure 15:
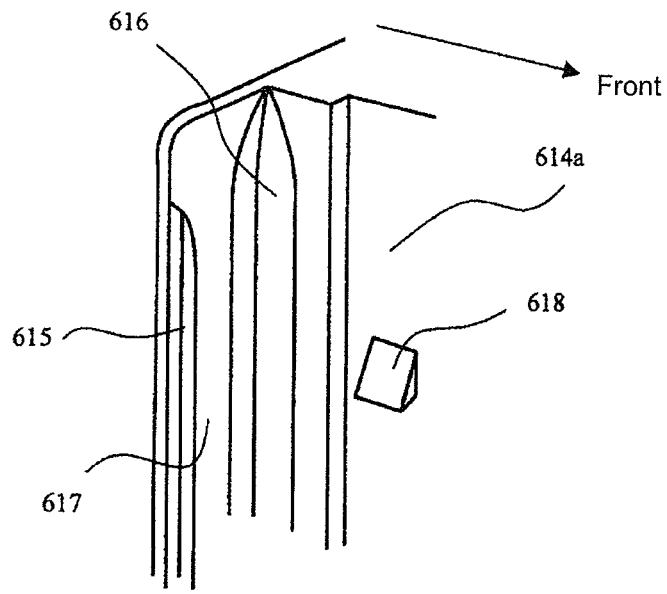
FIG. 15 is a perspective view showing the inside of the adapter receiver in FIG. 14.
Figure 16:
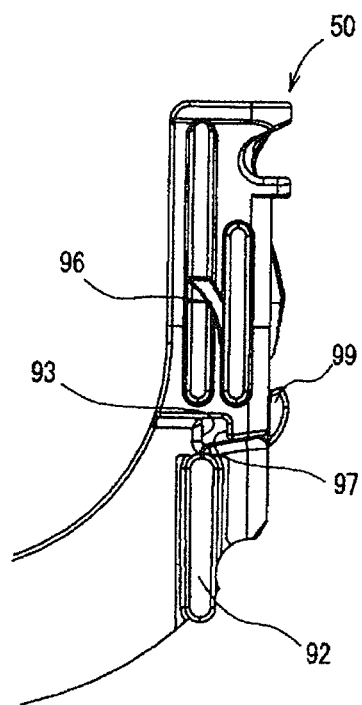
FIG. 16 is a diagram showing a rear face (arm portion) of the syringe holding member.

As shown in FIG. 14 and FIG. 15, a pair of engagement hooks 618, 618 is formed inside of the flange receiver 614a, for locking syringe holding member 50. Hooks 618 are formed to protrude toward the inside of the groove. As shown in FIG. 16, a vertical rib 92 is provided on a rear face of syringe holding member 50 (rear face of the arm portion) for insertion into the guide groove 617 described above. Engaging hooks 99 protruding outward for engaging with the hooks 618 of the adapter receiver 614a are formed on the outer surface of the arm portion.

The operation for mounting the syringe holding member 50 will be described. First, user pinches ends of the both arm portions so that the arm portions can elastically bend inward, and user puts it into the adapter receiver 614a.

The syringe holding member 50 is locked in the adapter receiver 614a, after an engagement of the hook 618 formed on adapter receiver 614a with the engaging hook 99 (see FIG. 16) on the arm portion. The insertion of the member 50 can be done smoothly, since the rib 92 on the rear face of syringe holding member 50 can be guided within the guide groove 617 of adapter receiver 614a Even if the syringe holding member is attempted to be insert in the opposite orientation (reversed front and back), the syringe holding member cannot be inserted into the adapter receiver because of the ribs 92 formed on the rear face of the syringe holding member. This can prevents user from mounting the holding member 50 in wrong orientation.

To demount the syringe holding member, contrary to the operation described above, user may pinch both arm portions of the syringe holding member to bend the respective arm portions inward so that the engagement of engaging hook 99 of the holding member and engagement hook 618 of the adapter receiver can be released. User then pulls it out from the receiver 614a.

As shown in FIG. 16, a inclined rib 96 may be formed on the rear face of the arm portion. The inclined rib 96 preferably is configured to abut on a top of a vertical rib 615 within the adapter receiver 614a when the arm portions are bent inward. The inclined surface is configured to slide on the top of vertical rib 615 to thereby generate an upward force against the syringe holding member 50. This causes the holding member 50 to be raised from the adapter receiver 614a to facilitate the removal of holding member 50.

To prevent the arm portion from being broken due to bending thereof more than a predetermined amount, a structure for limiting the inward bending amount of the arm portion may be provided. Specifically, abutting surfaces 93, 97 oppositely placed at an interval between them are provided for the base member and the movable member, respectively, these surfaces serve as a stopper. When the arm portion is bent inward (to the left in FIG. 16), the abutting surfaces 93, 97 contact to each other, to avoid further inward displacement of the arm portion. Such a construction can prevent breakage of the arm portion.

The arm portion is not limited to the structure in which arm portions 67, 67 (see FIG. 7) are bent by the elastic deformation of the member itself. Instead, for example, fixing portion 61A and arm portions 67, 67 may be formed of separate parts, being connected by a biasing member such as a spring. The arm portions 67, 67 are movable inward or outward, resisting the force of the biasing member.

While the construction shown in FIG. 7 has been described in the example in which only the surface on the back side of flange-receiving groove 77 exists, a front surface may be formed in the syringe holding member 50 so that a flange-receiving groove (having a concave cross section) can be provided by the syringe holding member itself.

Figure 17:
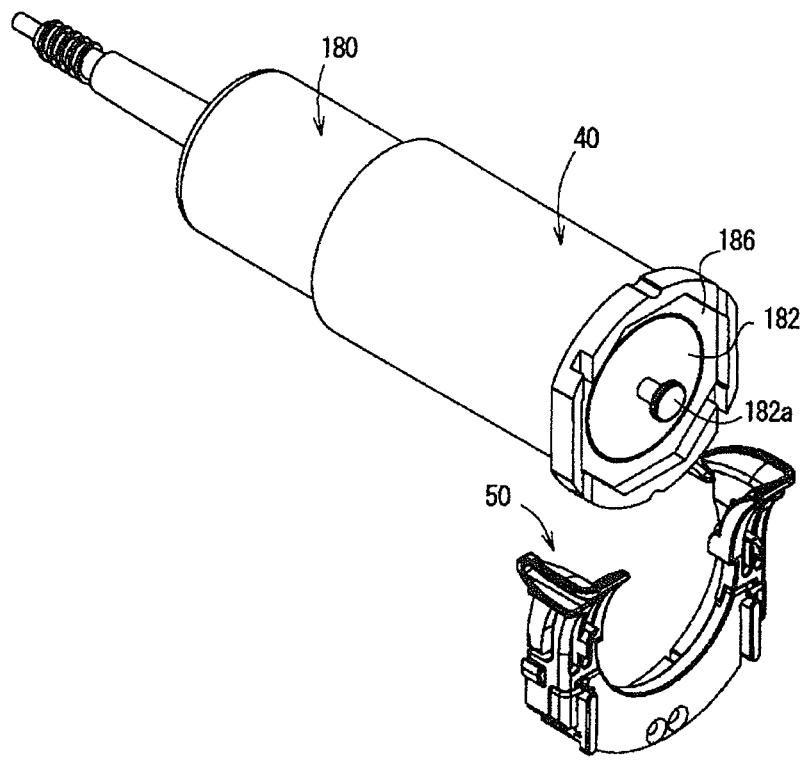
FIG. 17 is a perspective view showing another example of the syringe.
Figure 18:
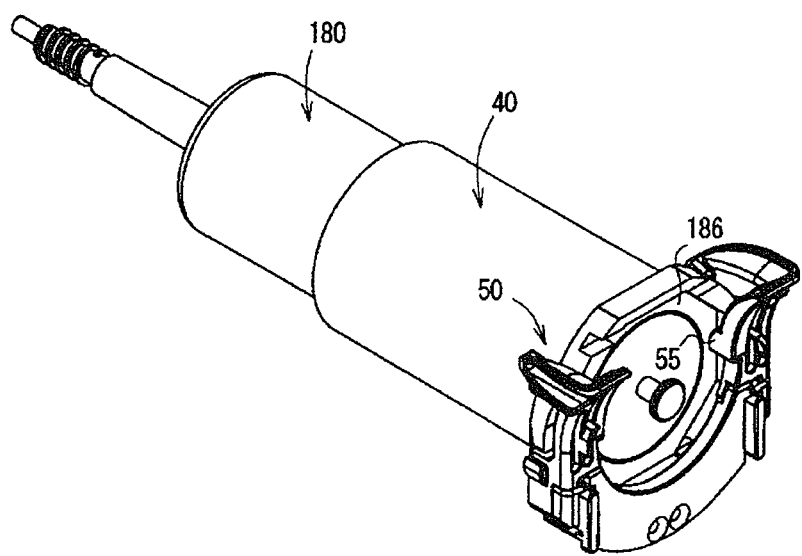
FIG. 18 is a perspective view showing the state in which the syringe in FIG. 17 is held on the syringe holding member with the adapter case interposed between them.

Various syringes can be used in the adapter case 40. For example, in syringe 180 shown in FIG. 17, a piston member 182 of a rod-less type is slidably inserted into a cylinder member. An engaging protrusion 182a, to be caught by a grasping structure (not shown) of the piston driving mechanism, may be formed on the rear face of piston member 182. In the syringe 180, a flange 186 of the cylinder member may be octagonal outline (by way of example) as in the embodiment described above. As shown in FIG. 18, in the state in which case 40 is held by the syringe holding member 50, the tips of ribs 55, 55 (only one of which is shown) of syringe holding member 50 abut on the rear face of flange 186 of syringe 180 as in the embodiment described above.

[Adapter Identifying Member]

The syringe holding member 50 as descried above serves as a syringe adapter for mounting various types of syringes on the injector. When a plurality of types of syringe adapters are used, it is convenient to allow the injection head to easily identify which of syringe adapters is mounted on the injection head, that is, which syringe is mounted on the injection head, and whether a syringe adapter is mounted or not. Thus, the syringe adapter preferably has an adapter identifying members to be used to identify the type of the syringe adapter.

The syringe adapter is formed to be able to have up to four subjects to be detected as the adapter identifying member (within reference numeral 69 in FIG. 7). At least one of the number, the positions, the material, and the attachment method of the subjects to be detected varies among the types of the syringe adapter.

On the other hand, the injection head has at least one sensor for individually detecting the subjects to be detected at the position opposite to the position where the subjects to be detected can be attached in the state in which the syringe adapter is mounted. A syringe mounted on the syringe holding member can be identified based on a combination of the subjects detected by the sensor. When any of the subjects to be detected is not detected at any position, it is determined that no syringe adapter is mounted.

The positions and the number of the subjects to be detected are not limited particularly and can be set as appropriate in view of the type of the syringe adapter mounted on the injection head. For example, when a small number of types of syringe adapters are intended to be used, the number of subjects to be detected can be reduced accordingly. When a large number of types of syringe adapters are used and cannot be dealt with by only the four subjects to be detected, the number of the subjects to be detected can be increased to more than four.

The adapter identifying member can be formed of various materials such as metal and plastic.

The sensor for detecting the adapter identifying member can be realized by using any sensor capable of detecting the adapter identifying member when the syringe adapter is appropriately mounted.

Particularly, a proximity sensor for detecting the presence or absence and the position of an object in a non-contact manner can be preferably used. A representative proximity sensor uses magnetism as a detection medium to detect the presence or absence and the position of an object. The types of the magnetism detected by the proximity sensor include a direct-current static magnetic field and an alternating-current magnetic field.

(1) When the proximity sensor using the direct-current magnetic field as the detection medium is used as the sensor, a magnet can be used as the adapter identifying member. As the proximity sensor capable of detecting the magnet, it is possible to use a semiconductor magnetic sensor such as a magnetic resistance element and a hall element, and a ferromagnetic sensor such as a flux gate type sensor, an MR (Magnet-Resistive) element, and an MI (Magneto-Impedance) element.

The proximity sensor for detecting the direct-current static magnetic field detects the polarity of the magnet. Thus, at least one magnet is placed as the adapter identifying member such that the orientation of the polarity is different for each type of the syringe adapter. Since the sensor detects the polarity of the magnet, it is possible to identify which syringe adapter is mounted from the combination of the detected polarities of the magnets. In this case, however, since the sensor detects the polarity of the magnet, correct detection cannot be performed if the magnet is attached with the polarity reversed due to errors in operation.

(2) On the other hand, in the proximity sensor using the alternating-current magnetic field as the detection medium, metal can be used as the adapter identifying member, and no problem occurs from the errors in operation as described above. In addition, since the proximity sensor using the alternating-current magnetic field as the detection medium can detect the adapter identifying member at a distance smaller than that of the proximity sensor using the direct-current static magnetic field as the detection medium, the former can detect that the syringe adapter is mounted at the normal position more correctly. Consequently, in the present invention, the proximity sensor using the alternating-current magnetic field as the detection medium is preferably used as the sensor for detecting the adapter identifying member.

The proximity sensor using the alternating-current magnetic field as the detection medium has a coil and takes advantage of the fact that passing a certain alternating current through the coil by an alternating-current power source to provide the alternating-current magnetic field for the metal (adapter identifying member) produces eddy currents in the metal. The eddy currents produced in the metal cause a magnetic field to produce an induced voltage in the coil. As a result, when the metal is brought closer to the coil, the impedance of the coil which is the ratio of the voltage produced in the coil to the current passed through the coil is changed. The proximity sensor uses the change in the impedance to detect the metal.

The proximity sensor of this type is broadly classified into a single coil type in which one coil has the function as an excitation coil providing the alternating-current magnetic field for the adapter identifying member and the function as a detection coil detecting the eddy current magnetic field produced from the adapter identifying member and a multi coil type in which a plurality of coils are provided.

Examples of the type of the proximity sensor of the single coil type include a high-frequency oscillation type and a filter type. The proximity sensor of the high-frequency oscillation type incorporates a detection coil in part of an oscillation circuit and detects a change in the oscillation amplitude or the oscillation frequency in accordance with a change in impedance. The proximity sensor of the filter type incorporates a detection coil in part of an LC or LR filter circuit and uses the fact that the filter characteristics vary with a change in impedance of the detection coil.

Examples of the types of the proximity sensor of the multi coil type include a double coil type, a differential coil type, and a fork coil type.

The proximity sensor of the double coil type uses two coils of the same structure, in which one of them is brought closer to the adapter identifying member as the detection coil and the other is used as a reference coil and placed to avoid any influence of the adapter identifying member. When the two coils are excited under the same conditions and the difference in induced voltage is compared, it can be said that the difference in the induced voltage between them is produced by the approach of the adapter identifying member since the detection coil is affected by the approach of the adapter identifying member. A detection circuit is typically realized by constructing an impedance bridge with the two coils and exciting it through a fixed oscillator to detect the amplitude of the unbalanced voltage or the phase to the exciting current. Alternatively, the unbalanced voltage obtained from the bridge circuit is amplified and fed back to the excitation side of the bridge circuit to oscillate the circuit, and the resulting amplitude is detected.

In the proximity coil of the differential coil type, typically, detection coils are placed at symmetric positions on both sides of an excitation coil, and the terminals of the detection coils are connected in the series with the reverse polarities and are used as a detection output end. Since the excited magnetic flux produces the equal induced voltage in the detection coils, the induced voltage due to the excited magnetic field is cancelled, and only the induced voltage due to the magnetic flux produced by eddy currents can be taken out similarly to the double coil type. Then, similarly to the double coil type, it is only required to detect the amplitude or the phase of the output voltage at the terminal of the detection coil, or to amplitude the voltage at the terminal of the detection coil, feed it back to the excitation coil, and oscillate it.

In the proximity sensor of the fork coil type, the excitation coil and the detection coil are placed opposite to each other to make magnetic coupling, and the adapter identifying member is inserted between them to detect a change in the amplitude or the phase of the induced voltage produced in the detection coil.

Description has been made of various proximity sensors capable of detecting the metal in a non-contact manner by using the alternating-current magnetic field as the detection medium. Any of them can be used in the present invention. When the proximity sensor capable of detecting the metal is used, the adapter identifying member may be formed of metal entirely or partially.

The size and the shape of the adapter identifying member can be arbitrarily set as long as it does not interfere with the mounting of syringe adapter 300. Preferably, the adapter identifying member may be a ball plunger.

When the ball plunger is used as the adapter identifying member, the ball plunger is preferably attached such that part of a ball thereof is protruded from the surface of syringe adapter 300. On the other hand, adapter receiver 114a is preferably provided with a concave portion or a through hole for accommodating the proximity sensor at the position opposite to the ball plunger in the state in which syringe adapter 300 is mounted on adapter receiver 114a such that the ball of the ball plunger engages with the concave portion or the through hole. This allows the adapter detecting means to have an auxiliary lock function of syringe adapter 300 to adapter receiver 114a.

As described above, the proximity sensor can be placed within the concave portion or the through hole formed in adapter receiver 114a. In this case, the proximity sensor may be held through press fit into the concave portion or the through hole or may be held through screwing. The holding of the proximity sensor through screwing can facilitate the position adjustment of the proximity sensor within the concave portion or the through hole and the removal of the proximity sensor for replacing. The concave portion or the through hole may be filled with resin. This can increase resistance to water of the proximity sensor to reduce the possibility of a failure of the proximity sensor when the chemical liquid or the like is attached thereto.

1 Injector
10, 80, 180 Syringe
11, 81 Cylinder Member
15 Notch
16, 86, 186 Flange
17 Cut-Portion
40 Adapter Case
41 Cylindrical Portion
43 Concave Portion
45 Notch
47 Cut-Portion
49 Vertical Groove
50 Syringe Holding Member
51 Base Member
55 Rib
61 Movable Member
61a Fixing Portion
67 Arm Portion
68 Screw Hole
77 Flange Receiving Groove
96 Inclined Rib
99 Engaging Hook

The invention claimed is:

1. A syringe holding structure, comprising:
an adapter case comprising:
a cylindrical portion, wherein the cylindrical portion is configured to receive a barrel portion of a syringe in an axis direction, and wherein the cylindrical portion covers a whole circumference of the syringe, and
a flange portion formed at one end of the cylindrical portion, wherein the outer circumference of the flange portion has a pair of notches, wherein the flange portion is configured to receive a flange of the syringe in an axis direction, wherein a rear face of the flange portion comprises a concave portion configured to receive the flange of the syringe and fix the position of the syringe in the adapter case in a circumferential direction; and
a syringe holder comprising:
an arc-shaped base member, a U-shaped movable member comprising a pair of arm portions, a flange-receiving groove configured to receive the flange portion of the adapter case, wherein the flange portion of the adapter case has a pair of vertical grooves in the circumferential direction on a rear face and wherein the flange portion of the adapter case is configured to be inserted transversely into the flange-receiving groove of the syringe holder, wherein the syringe holder further comprises a pair of ribs protruding into the flange-receiving groove, one rib from each of the pair of arm portions, wherein each rib is configured to fit into one vertical groove of the pair of vertical grooves of the adapter case, the vertical grooves being vertical in their entirety, wherein the pair of ribs abut a rear face of the flange of the syringe when the syringe is mounted in the syringe holder via the adapter case and fix the position of the syringe with respect to the adapter case,
wherein each arm portion of the pair of arm portions comprises a hooked plate spring, wherein each hooked plate spring is configured to engage a notch of the pair of notches when the flange portion is rotated by 90 degrees about its axis in the flange receiving groove and fix the position of the flange portion in a circumferential direction.

2. The syringe holding structure according to claim 1, wherein the concave portion has a depth proportional to a thickness of the flange portion.

3. The syringe holding structure according to claim 1, wherein the flange of the syringe has a polygonal outline shape.

4. The syringe holding structure according to claim 1, wherein the syringe holder includes one or more adapter is configured to identify a type of the syringe holder.

5. The syringe holding structure of claim 1, wherein the syringe holding structure is detachably mounted on an injector head in a side-loading manner.

6. A chemical liquid injector comprising a syringe holding structure, wherein the syringe holding structure comprises:
- an adapter case comprising:
  - a cylindrical portion, wherein the cylindrical portion is configured to receive a barrel portion of a syringe in an axis direction, and wherein the cylindrical portion covers a whole circumference of the syringe, and
  - a flange portion formed at one end of the cylindrical portion, wherein the outer circumference of the flange portion has a pair of notches, wherein the flange portion is configured to receive a flange of the syringe in an axis direction, wherein a rear face of the flange portion comprises a concave portion configured to receive the flange of the syringe and fix the position of the syringe in the adapter case in a circumferential direction; and
- a syringe holder comprising:
  - an arc-shaped base member, a U-shaped movable member comprising a pair of arm portions, a flange-receiving groove configured to receive the flange portion of the adapter case, wherein the flange portion of the adapter case, wherein the flange portion of the adapter case has a pair of vertical grooves in the circumferential direction on a rear face and wherein the flange portion of the adapter case is configured to be inserted transversely into the flange-receiving groove of the syringe holder, wherein the syringe holder further comprises a pair of ribs protruding into the flange-receiving groove, one rib from each of the pair of arm portions, wherein each rib is configured to fit into one vertical groove of the pair of vertical grooves of the adapter case, the vertical grooves being vertical in their entirety, wherein the pair of ribs abut a rear face of the flange of the syringe when the syringe is mounted in the syringe holder via the adapter case and fix the position of the syringe with respect to the adapter case,
  - wherein each arm portion of the pair of arm portions comprises a hooked plate spring, wherein each hooked plate spring is configured to engage a notch of the pair of notches when the flange portion is rotated by 90 degrees about its axis in the flange receiving groove and fix the position of the flange portion in a circumferential direction.

7. The chemical liquid injector of claim 6, further comprising one or more syringes.

8. The chemical liquid injector of claim 7, wherein said syringe is a pre-filled type syringe.

9. The chemical liquid injector of claim 7, wherein said syringe is an empty syringe.

* * * * *

UNITED STATES PATENT AND TRADEMARK OFFICE
CERTIFICATE OF CORRECTION

PATENT NO. : 10,383,995 B2
APPLICATION NO. : 13/260222
DATED : August 20, 2019
INVENTOR(S) : Shigeru Nemoto Page 1 of 1

It is certified that error appears in the above-identified patent and that said Letters Patent is hereby corrected as shown below:

In the Specification

Column 1, Line 10 (approx.), change "2009The" to --2009. The--.

Column 2, Line 23, after "direction" insert --.--.

In the Claims

Column 13, Lines 21-22, in Claim 6, after "case," delete "wherein the flange portion of the adapter case,".

Signed and Sealed this
Twenty-fourth Day of March, 2020

Andrei Iancu
*Director of the United States Patent and Trademark Office*